United States Patent [19]
Barth et al.

[11] Patent Number: 6,143,903
[45] Date of Patent: Nov. 7, 2000

[54] PROCESS FOR THE PRODUCTION OF ENANTIOMERICALLY-PURE AZETIDINE-2-CARBOXYLIC ACID

[75] Inventors: Philipp Barth, Zürich; Armin Pfenninger, Uetikon, both of Switzerland

[73] Assignee: Astra Aktiebolag, Sodertalje, Sweden

[21] Appl. No.: 08/913,016

[22] PCT Filed: Apr. 22, 1997

[86] PCT No.: PCT/SE97/00675

§ 371 Date: Sep. 4, 1997

§ 102(e) Date: Sep. 4, 1997

[87] PCT Pub. No.: WO97/41084

PCT Pub. Date: Nov. 6, 1997

[30] Foreign Application Priority Data

Apr. 26, 1996 [SE] Sweden ................................. 9601600

[51] Int. Cl.$^7$ ...................... C07D 205/04; C07B 57/00
[52] U.S. Cl. ............................................................. 548/953
[58] Field of Search ............................................. 548/953

[56] References Cited

U.S. PATENT DOCUMENTS

| | | | |
|---|---|---|---|
| 5,880,291 | 3/1999 | Ushio et al. | 548/943 |
| 5,942,630 | 8/1999 | Barth et al. | 548/943 |

FOREIGN PATENT DOCUMENTS 0416736  3/1991  European Pat. Off. .

OTHER PUBLICATIONS

White et al, J. Coord. Chem., vol. 6, pp. 53–57, 1976.

Fowden, L., "Azetidine–2–carboxylic Acid; a New Cyclic Imino Acid Occurring in Plants", (1956), BioChem J., vol. 64, 323–332.

Yamada et al, "Method for the Racemization . . . ," J. Org. Chem., vol. 48, pp. 843–846 (1983).

Shiraiwa et al, I,"Asymmetric Transformation of (RS)–Cysteine . . . ," Bull. Chem. Soc. Jpn., vol. 62, pp. 109–113; (1989).

Yoshioka et al, "The Optical Resolution and Asymmetric . . . ," Bull. Chem. Soc. Jpn., vol. 60, pp. 649–652 (1987).

Hongo et al, "Assymetric Transformation of DL–p–Hydroxyphenylglycine . . . ," Bull. Chem. Soc. Jpn., vol. 58, pp. 433–436 (1985).

Grigg et al, "The Mechanism of the Racemisation . . . ," Tetrahedron Letters, vol. 24, No. 41, pp. 4457–4460 (1983).

Clark et al, "A New Asymmetric Transformation," J.C.S. Perkin I, pp. 475–481 (1976).

Shiraiwa et al, II,"Assymmetric Transformation of Proline . . . ," Bull. Chem. Soc. Jpn., vol .64, pp. 3251–3255 (1991).

J. Heterocyclic. Chem., (1969), vol. 6, p. 993. Rodebaugh et al. R.

Bull. Chem. Soc. Japan, (1973), vol. 46, No. 2, p. 699–700, Yokoyama et al.

Biochem J., (1956), vol. 64, p. 373., Ormerod.

*Primary Examiner*—Floyd D. Higel
*Attorney, Agent, or Firm*—Nixon & Vanderhye

[57] ABSTRACT

The invention relates to a process for the production of enantiomerically-pure AzeOH which comprises selective crystallisation of a diastereomerically-pure AzeOH-tartrate salt from a homogeneous solution of AzeOH, optically-active tartaric acid, an organic acid and an aldehyde, followed by liberation of the free amino acid.

18 Claims, No Drawings

PROCESS FOR THE PRODUCTION OF ENANTIOMERICALLY-PURE AZETIDINE-2-CARBOXYLIC ACID

This application is a 371 of PCT/SE97/00675, filed Apr. 22, 1997.

FIELD OF THE INVENTION

This invention relates to a process for the production of enantiomerically pure azetidine-2-carboxylic acid.

PRIOR ART

L-Azetidine-2-carboxylic acid (L-AzeOH) is known to be useful in the synthesis of inter alia high molecular weight polypeptides and in particular as an analogue of the well known amino acid proline.

Previously documented preparations of enantiomerically-pure AzeOH (i.e. D- and/or L-AzeOH) from the racemate (DL-AzeOH) involve long and relatively complicated multi-step methodology.

A four step preparation involving the protection, resolution and subsequent deprotection of DL-AzeOH is known from J. Heterocyclic Chem. (1969) 6, 993. In this method, N-carbobenzoxy-protected DL-AzeOH is resolved using L-tyrosine hydrazide as resolution agent, and then isolated before a final deprotection step. This process has the further disadvantage that L-tyrosine hydrazide is expensive.

Other reported preparations of L-AzeOH include a five step preparation via homoserine lactone, starting from N-tosyl protected L-methionine (see e.g. Japanese Patent Application No. 14457/74 and Bull. Chem. Soc. Jpn. (1973) 46, 669) and a five step preparation via L-4-amino-2-chlorobutyric acid, starting from L-2,4-diaminobutyric acid (see Biochem. J. (1956) 64, 323).

DESCRIPTION OF THE INVENTION

Tartaric acid has been known for many years to exist in three stereochemical forms, the L-form, the D-form and the meso-form. Two of these diastereoisomers, L- and D-tartaric acid are enantiomers.

We have now surprisingly found that one enantiomer of AzeOH may be converted to the other in an enantiomerically-pure form and in extremely high yields via a novel and efficient process which comprises the selective crystallisation of a diastereomerically-pure AzeOH-tartrate salt from a mixture of AzeOH, optically-active tartaric acid, an organic acid and an aldehyde, followed by liberation of the free amino acid.

In particular, we have found that selective crystallisation of AzeOH with D-tartaric acid, under anhydrous conditions in the presence of an organic acid and an aldehyde produces extremely high yields of diastereomerically-pure L-AzeOH-D-tartrate in the crystalline form, from which optically-pure L-AzeOH may be liberated. Similarly, crystallisation using L-tartaric acid produces extremely high yields of diastereomerically-pure D-AzeOH-L-tartrate, from which optically-pure D-AzeOH may be liberated.

According to the invention there is provided a process for the production of enantiomerically-pure AzeOH which comprises:

(a) selective crystallisation of a diastereomerically-pure AzeOH-tartrate salt from a homogeneous solution of AzeOH, optically-active tartaric acid, an organic acid and an aldehyde; followed by (b) liberation of the free amino acid, hereinafter referred to as "the process according to the invention", By "optically active" tartaric acid we mean D- or L-tartaric acid or a mixture thereof. However, we prefer that the D- or L-tartaric acid which is used in the process according to the invention is enantiomerically pure, for example with an optical purity (enantiomeric excess; e.e.) of greater than 95%.

The process according to the invention may be used to produce diastereomerically-pure AzeOH-tartrate salts from mixtures of AzeOH including racemic AzeOH or enantiomerically-enriched AzeOH.

By "enantiomerically-enriched" we mean any mixture of the isomers of is AzeOH in which one isomer is present in a greater proportion than the other.

Moreover, the process according to the invention may be used to convert one enantiomer of AzeOH to the other.

According to a second aspect of the invention there is provided a process for the conversion of one enantiomer of AzeOH to the other which comprises:

(a) for conversion of D-AzeOH to L-AzeOH, selective crystallisation of a diastereomerically-pure L-AzeOH-D-tartrate salt from a homogeneous solution of D-AzeOH, D-tartaric acid, an organic acid and an aldehyde, followed by liberation of the free amino acid; or (b) for conversion of L-AzeOH to D-AzeOH, selective crystallisation of a diastereomerically-pure D-AzeOH-L-tartrate salt from a homogeneous solution of L-AzeOH, L-tartaric acid, an organic acid and an aldehyde, followed by liberation of the free amino acid.

Although the process according to the invention may be used to produce either L-AzeOH-D-tartrate or D-AzeOH-L-tartrate with a diastereomeric excess (d.e.) greater than 90%, by "diastereomerically-pure AzeOH-tartrate salt" we mean a AzeOH-tartrate salt with a d.e. of greater than 40%.

Although the process according to the invention may be used to produce either L-AzeOH or D-AzeOH with optical purities (enantiomeric excess; e.e.) of greater than 90%, by "enantiomerically-pure AzeOH" we mean an AzeOH enantiomer with an e.e. of greater than 50%.

Suitable organic acids for use in the process according to the invention include $C_{1-8}$ mono- or difunctional carboxylic acids which may be linear or branched and may include further functional groups (e.g. hydroxy, halo, nitro or an aromatic ring, such as phenyl). Examples of suitable organic acids include formic acid and acetic acid. The organic acid may be used as a solvent system for dissolving the AzeOH, tartaric acid and aldehyde.

Suitable aldehydes for use in the process according to the invention include $C_{3-8}$ mono- or difunctional aldehydes which may be linear or branched and may include further functional groups (e.g. hydroxy, halo, nitro or an aromatic ring, such as phenyl). Examples of suitable aldehydes include butyric aldehyde and caproic aldehyde.

Suitable molar ratios of aldehyde to enantiomerically-enriched AzeOH are in the range 0.01:1.0 to 1.0:1.0, preferably 0.01:1.0 to 0.2:1.0 and particularly 0.05:1.0 to 0.1:1.0.

Suitable molar ratios of L- or D-tartaric acid to AzeOH which may be employed are in the range 0.5:1.0 to 2.0:1.0, preferably 0.6:1.0 to 1.1:1.0 and particularly 0.8:1.0 to 1.0:1.0.

Following dissolution of AzeOH and L- or D-tartaric acid in the solvent system, the mixture may, if necessary, be adjusted to form a homogeneous solution by appropriate means, for example by heating to elevated temperature (e.g. at reflux).

Crystallisation of the diastereomerically-pure AzeOH-tartrate salt is achieved by cooling the solution of AzeOH and tartaric acid to supersaturation temperature. Final crystallisation temperatures for the above mentioned solvent systems are typically in the range −10 to 30° C., for example −5 to 10° C. and preferably 0 to 5° C.

Crystallisation may be effected with or without seeding with crystals of the appropriate diastereomerically-pure AzeOH-tartrate salt. However, we prefer crystallisation to be effected by seeding.

The crystalline salt may be isolated using techniques which are well known to those skilled in the art, for example decanting, filtering or centrifuging.

Liberation of the enantiomerically-pure free amino acid from the crystalline salt following selective crystallisation may be achieved by displacing tartaric acid from the AzeOH-tartrate salt by reacting with a carbonate, an oxide, a hydroxide or a chloride of a metal which is known to form salts with tartaric acid (eg calcium or potassium). Particularly preferred calcium salts include calcium chloride. Particularly preferred potassium salts include potassium hydroxide. The displacement reaction may be performed above room temperature (eg between 30 and 60° C.) in the presence of an appropriate solvent in which AzeOH is soluble and the metal-tartrate salt is poorly soluble (eg water). Free optically pure amino acid may be separated from the precipitated metal tartrate (or hydrogen tartrate) by conventional techniques (eg filtering, centrifuging or decanting).

Enantiomerically-pure D- or L-AzeOH may be further purified using conventional techniques (e.g. recrystallisation from an appropriate solvent, such as acetone or water, or combinations thereof).

The process according to the invention may also be used to optically enrich optically impure AzeOH-tartrate salts.

The process according to the invention has the advantage that enantiomerically pure AzeOH may be prepared in higher yields, with greater optical purity, in a manner which involves fewer steps (and without the need for protecting groups), in less time, more conveniently and at a lower cost than processes previously employed for the production of enantiomerically pure AzeOH. Moreover, tartaric acid may be recovered from the process according to the invention in a form which is pure enough for further use in the process (i.e. tartaric acid may be recycled without the need for additional purification).

The invention is illustrated, but in no way limited, by the following examples. The crystalline products were analysed for AzeOH content by non-aqueous titration with perchloric acid. Optical purity was determined using HPLC on a chiral column.

EXAMPLES

Preparation of Diastereomerically-Pure AzeOH-Tartrate Salts

Example 1

L-AzeOH (99% e.e.; 1.01 g; 10 mmol) was dissolved in formic acid (4 mL) at 80° C. Butyric aldehyde (0.072 g; 1.0 mmol) was added and the mixture heated at 90° C. for 3 hours. The solvent was subsequently distilled (45° C.; 4 mbar) and the residue dried under vacuum. The residue was subsequently dissolved in a mixture of ethanol:water (35.6: 29.1) at 76° C. L-Tartaric acid (1.5 g; 10 mmol) was added, the insoluble compounds were filtered off and the solution was cooled to 0° C. The crystalline product was filtered, washed and dried under vacuum to yield 0.45 g of D-AzeOH-L-tartrate with a d.e. of 75%.

Example 2

50 g of a mother liquor containing enantiomerically-enriched AzeOH containing 16 g (68% e.e.) of D-AzeOH (prepared in accordance with Example 1) was concentrated under vacuum to give a viscous oil, which was further dewatered by azeotropic distillation with isopropanol. Acetic acid (72 mL) was added to the concentrated residue. The mixture was heated to 95° C. and D-tartaric acid (25 g) and caproic aldehyde (2.8 g) were added. The mixture was seeded with L-AzeOH-D-tartrate, kept at 95–100° C. for 3 hours and then gradually cooled to 0° C. The crystalline product was filtered, washed and dried at 60° C. under vacuum to yield 29.3 g of L-AzeOH-D-tartrate with a d.e. of 94.6%. Recrystallisation of 28 g of the diastereomeric salt from ethanol:water (140 mL; 1.25:1.0) yielded 21.4 g of L-AzeOH-D-tartrate with a d.e. of 100%.

Example 3

DL-AzeOH (6.14 g; 60.8 mmol) was dissolved in acetic acid (36.5 mL) at 85° C. Butyric aldehyde (0.49 g; 6.8 mmol) and D-tartaric acid (9.12 g; 60.8 mmol) were added and the mixture maintained at 85° C. for 6 hours. The reaction mixture was then gradually cooled to 0 C. The crystalline product was filtered off, washed with acetic acid and dried to yield 13.78 g (90%) of L-AzeOH-D-tartrate with a d.e. of 89%. Recrystallisation 13.78 g of the diastereomeric salt from dissolved acetic acid:water (9:1; 124 mL) yielded 11.08 g of L-AzeOH-D-tartrate with a d.e. of 99.8%.

Example 4

The method described in Example 3 may be used to prepare of D-AzeOHL-tartrate using L-tartaric acid instead of D-tartaric acid.

Preparation of L-Azetidine-2-Carboxylic Acid (L-AzeOH)

Example 5

L-AzeOH-D-tartrate (7.2 g; 28 mmol; d.e. of 99%) was dissolved in hot water (16 mL). At about 45° C., aqueous potassium hydroxide (6 mL; 6 M; 24 mmol) was added over 15 minutes. The solution was cooled to 5° C. at which temperature potassium hydrogen tartrate was formed, which was filtered and washed with cold water (3 mL). The combined filtrate was concentrated under vacuum to give a crude product which was stirred for 1 hour at 60° C. with water (1 mL) and acetone (30 mL). The product was filtered off and dried to yield 2.5 g (89%) of L-AzeOH with an e.e. of 99%.

What is claimed is:

1. A process for the production of enantiomerically-pure AzeOH which comprises:
    (a) selective crystallisation of a diastereomerically-pure AzeOH-tartrate salt from a homogeneous solution of AzeOH, optically-active tartaric acid, an organic acid and an aldehyde; followed by
    (b) liberation of the free amino acid.

2. A process for the conversion of one enantiomer of AzeOH to the other which comprises:
    (a) for conversion of D-AzeOH to L-AzeOH, selective crystallisation of a diastereomerically-pure L-AzeOH-D-tartrate salt from a homogeneous solution of D-AzeOH, D-tartaric acid, an organic acid and an aldehyde, followed by liberation of the free amino acid; or (b) for conversion of L-AzeOH to D-AzeOH, selective crystallisation of a diastereomerically-pure D-AzeOH-L-tartrate salt from a homogeneous solution of L-AzeOH, L-tartaric acid, an organic acid and an aldehyde, followed by liberation of the free amino acid.

3. A process as claimed in claims 1 or claim 2, characterised in that the organic acid is used as solvent.

4. A process as claimed in any one of claims 1 to 3, characterised in that the organic acid is a $C_{1-8}$ mono- or difunctional carboxylic acid.

5. A process as claimed in claim 4, characterised in that the organic acid is formic acid or acetic acid.

6. A process as claimed in any one of claims 1 to 5, characterised in that the aldehyde is a $C_{3-8}$ mono- or difunctional aldehyde.

7. A process as claimed in claim 6, characterised in that the aldehyde is butyric aldehyde or caproic aldehyde.

8. A process as claimed in any one of claims 1 to 7, characterised in that the molar ratio of aldehyde to enantiomerically-enriched AzeOH is in the range 0.01:1.0 to 1.0:1.0.

9. A process as claimed in claim 8, characterised in that the molar ratio is in the range 0.01:1.0 to 0.2:1.0.

10. A process as claimed in claim 9, characterised in that the molar ratio is in the range 0.05:1.0 to 0.1:1.0.

11. A process as claimed in any one of claims 1 to 10, characterised in that the molar ratio of L- or D-tartaric acid to azetidine-2-carboxylic acid in the range 0.5:1.0 to 2.0:1.0.

12. A process as claimed in claim 11, characterised in that the molar ratio is in the range 0.6:1.0 to 1.1:1.0.

13. A process as claimed in claim 12, characterised in that the molar ratio is in the range 0.8:1.0 to 1.0 to 1.0.

14. A process as claimed in any one of claims 1 to 13, characterised in that the selective crystallisation is achieved by cooling to a temperature in the range −10 to 30° C.

15. A process as claimed in claim 14, characterised in that the temperature is in the range −5 to 10° C.

16. A process as claimed to claim 15, characterised in that the temperature is in the range 0 to 5° C.

17. A process as claimed in any one of claims 1 to 16, characterised in that the free amino acid is liberated by displacement of tartaric acid using calcium chloride.

18. A process as claimed in any one of claims 1 to 16, characterised in that the free amino acid is liberated by displacement of tartaric acid using potassium hydroxide.

* * * * *